United States Patent [19]

Johnasen et al.

[11] Patent Number: 5,045,636

[45] Date of Patent: Sep. 3, 1991

[54] LOW CLOSURE FORCE EMI/RFI SHIELDED DOOR

[75] Inventors: Eivind Johnasen, Weare, N.H.; James McQueeney, Natick, Mass.

[73] Assignee: Chomerics, Inc., Woburn, Mass.

[21] Appl. No.: 362,194

[22] Filed: Jun. 6, 1989

[51] Int. Cl.$^5$ .......................... H05K 9/00; E05F 1/04
[52] U.S. Cl. ................................ 174/35 MS; 49/239; 174/35 GC
[58] Field of Search ................ 49/239, 236, 237, 238; 174/35 MS:35 GC, 35 R

[56] References Cited

U.S. PATENT DOCUMENTS

| | | | |
|---|---|---|---|
| 989,219 | 4/1911 | Winter | 49/238 |
| 3,437,735 | 4/1969 | Schaller, Jr. | 174/35 MS |
| 4,571,449 | 2/1986 | Lindenberger et al. | 174/35 |
| 4,590,710 | 5/1986 | Newland | 49/478 |
| 4,656,312 | 4/1987 | Mallott | 174/35 |
| 4,677,251 | 6/1987 | Merewether | 174/35 |
| 4,710,590 | 12/1987 | Ekdahl | 174/35 |
| 4,740,654 | 4/1988 | Lindgren | 174/35 |
| 4,786,758 | 11/1988 | Zielinski | 174/35 GC |

FOREIGN PATENT DOCUMENTS 513654 11/1920 France .................................. 49/239

Primary Examiner—Philip C. Kannan
Attorney, Agent, or Firm—John Dana Hubbard; William L. Baker

[57] ABSTRACT

An EMI/RFI shielded door assembly for use in controlling the movement of EMI/RFI in a shielded room or enclosure. The assembly has an electrically conductive frame defining a generally rectangular opening. A conductive door stop is formed on the inner surfaces of the top and side members of the frame to form a pocket into which a shielded door may be held when in its closed position. The threshold of the frame is preferably flat. A series of cam or drop hinges are used to mount the door to the frame. The hinges cause the door to be raised or lowered to or from the threshold as it is rotated on the hinges from a closed to an open position and vice versa. A low closure force gasket, e.g. less than 5 pounds per linear inch preferably formed of a conductive elastomer, is used to fill any gap that may exist between the door and the frame. Optionally, a rotatable EMI/RFI shielding means mounted in a hollow of the bottom of the door and comprised of a flap or flipper like blade attached to a rotatable rod can be used to seal the gap between the door and the threshold.

17 Claims, 3 Drawing Sheets

LOW CLOSURE FORCE EMI/RFI SHIELDED DOOR

The present invention relates to a shielded door assembly. More preferably the present invention relates to a shielded door assembly having a low closure force characteristic and a low threshold along the bottom of the door.

BACKGROUND OF THE INVENTION

Shielded enclosures, e.g. rooms which prevent the ingress or egress of RFI or EMI signals have become increasingly more commonplace in the past few years.

This has in part been spurred by the increased awareness of the problems caused by stray or unwanted RFI and EMI signals as well as for security reasons. Typically, such enclosures are used as computer rooms, communication facilities, test chambers or medical rooms.

A shielded entrance, such as a door, is needed in each enclosure to allow for the transfer of personnel and equipment to and from the enclosure. Typically, such doors have been large, heavy, solid metal structures. A shielding means surrounding the door frame has generally consisted of metal finger stock, such as beryllium copper finger stock. Additionally, such doors typically have a raised threshold along the bottom of the door frame so that the finger stock may be used around the entire perimeter of the door.

Experience has shown that such doors require extensive maintenance, in that the metal finger stock tends to set (i.e., become permanently deformed), which reduces its shielding capabilities and necessitates replacement. Additionally, the finger stock often breaks due to metal fatigue and is also subject to corrosion and excessive wear caused by the frequent opening and closing of the door. Further, the force needed to properly close and form a conductive pathway around the entire door is excessively high when using metal finger stock. Likewise, the raised threshold is difficult to traverse, making the movement of equipment a difficult and time-consuming task. The use of inclined ramps or lifts may be needed for the movement of heavy equipment into and out of such enclosures. Lastly, such doors are often left open by its occupants to avoid the problems in repeatedly opening and closing such doors. This practice voids the purpose of the enclosure.

The present invention provides a new and unique shielded door assembly which eliminates the problems associated with finger stock and a raised threshold. The shielded door assembly of the present invention reduces the required closing force as well as eliminates the high threshold while maintaining its shielding integrity.

SUMMARY OF THE INVENTION

The present invention provides a shielded door which permits opening and closing of the access way through the use of minimal amounts of force.

Additionally, it provides a shielded door which eliminates the requirement of a raised threshold.

More specifically, the present invention provides a shielded door assembly for closing an opening in a shielded enclosure comprising a frame, a threshold, a doorstop attached to the frame and forming a recess into which a door may pivotably move so as to close off the opening in the enclosure, the doorstop having a resilient, conductive gasket, with low closure force characteristics, retained along its length and adapted to be in contact with the door when the door is in its closed position. A means for raising and the lowering the door as it pivotably moves from a closed to opened position so that when in a closed position the door is adjacent the threshold of the frame. The preferred means for raising and lowering the door is a series of cam or drop hinges. Lastly, a conductive sealing member contained along the bottom of the door which member is adapted to form a conductive seal between the door and the threshold when the door is in its closed position.

The means for forming a conductive pathway between the bottom of the door and the threshold preferably comprises a rotatable conductive blade preferably mounted within a recess of the door, which blade is capable of being rotated so that it establishes and maintains an electrical connection between the door and the threshold when the door is in its closed position.

The present invention provides a shielded door assembly that requires minimal amounts of closure force to secure the door in place and which eliminates the need for a raised threshold. The present invention overcomes many of the problems encountered with previous shielded door assemblies and does so in an efficient and economical way.

DETAILED DESCRIPTION OF THE INVENTION

Figure 1:
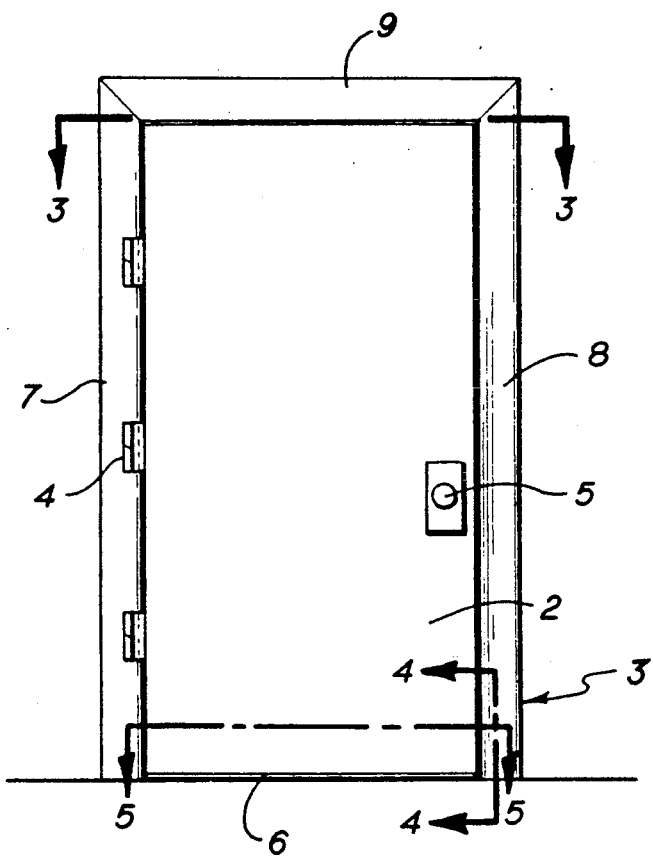
FIG. 1 is a front elevational view of a shielded door assembly according to the present invention, mounted to an enclosure and shown in its closed position.

FIG. 1 shows a door assembly 1 mounted to an enclosure. The assembly is comprised of a door 2 generally rectangular in shape, mounted to a frame 3 generally rectangular in shape, by a series of hinges 4. The door 2 can be secured in a closed position to the frame 3 by a suitable lock set 5. The frame 3 consists of a threshold 6, two side frame members, 7 and 8, and a top member 9 which interconnects the side members 7 and 8. The threshold 6 and top member 9 are spaced apart and parallel to each other. The side members 7 and 8 are also spaced apart and parallel to each other a well as being perpendicular to the threshold 6 and top member 9. The door 2, as shown, is mounted by its hinges 4 to the side portion 7 while the lock set 5 interacts with the side portion 8. Of course, the hinges and lock set could be mounted in the opposite direction so that the door could open to the right rather than to the left, as shown.

The hinges are preferably a "cam" or "drop" type of hinge. These hinges are designed so that the door moves in a vertical direction as the door is rotated on these hinges. This allows the door in its closed position to be close to or touching the surface of the threshold 6 of the frame 3. As the door 2 is opened, the two portions of the hinges ride against each other such that the door is lifted upwardly away from the threshold 6. Likewise, as the door is closed, the hinge portions ride downwardly against each other, causing the door to move toward the threshold.

An additional advantage of the cam hinges is that the hinges tend to make the door self-closing, thereby reducing the likelihood that the door would be left open by the enclosure's occupants.

Figure 2:
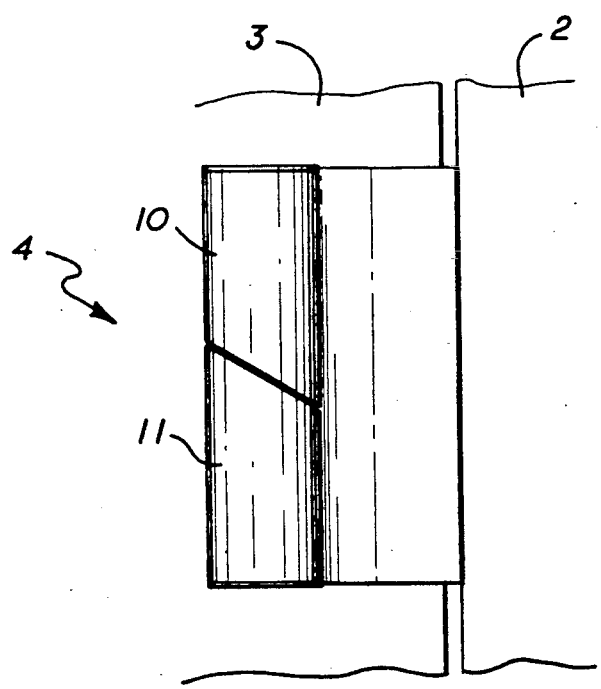
FIG. 2 is a close up view of a hinge of FIG. 1.

FIG. 2 shows one of these hinges as mounted between the door 2 and the frame 3. As can be seen, the hinge is made of two portions, 10 and 11. The surfaces of those two Portions which meet each other are angled respective to the horizontal plane of the hinges so that the vertical movement of the door can occur.

If necessary, the top member 9 of the door frame and/or the top portion of the door may be beveled at the portion meeting the door, so as to allow for the vertical movement of the door as it is opened and closed.

Figure 3:
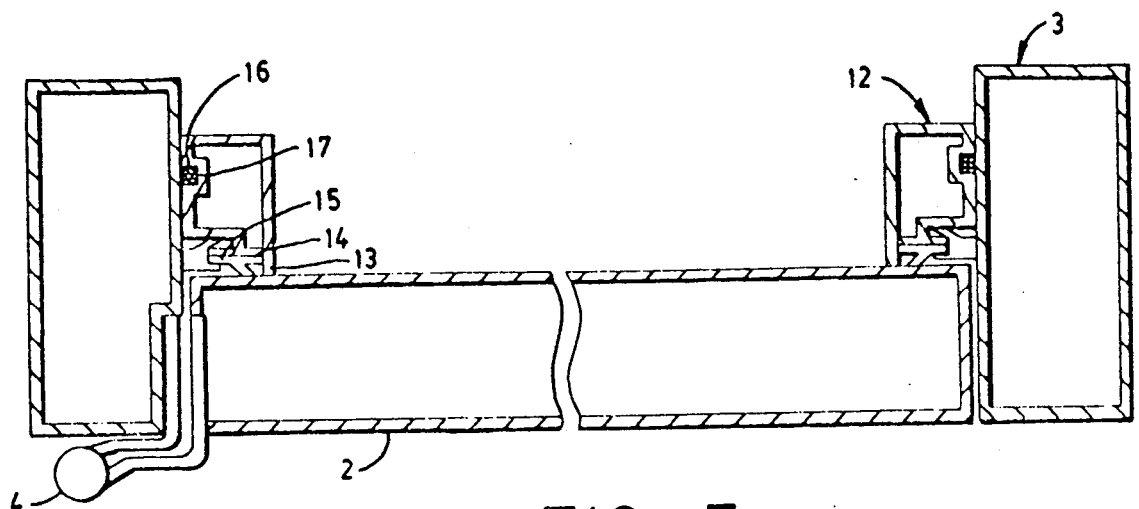
FIG. 3 is a fragmentary cross sectional view taken along the section 3—3 of FIG. 1 as viewed from above.

FIG. 3 shows the door assembly in more detail. The door 2 fits between the side frame members 7 and 8 and rests against a door stop 12 which is respectively attached to the inner surface of the side frame members 7 and 8 and the top frame member 9. The door stop 12 contains a compression stop 13 which limits the inward movement of the door 2 and a first recess 14 in which a conductive gasket 15 having a low closure force characteristic can be mounted.

The door stop 12 may be secured to the frame 3 by mechanical means such as screws or bolts or it may be secured to the frame 3 by welding. Preferably, the door stop 12 is welded to the frame by a continuous weld line rather than by spot welding to insure continuous conductivity between the frame 3 and the door stop 12. To insure that conductivity is maintained between the frame 3 and the door stop 12, a conductive wire mesh gasket 16 is compressibly secured between the frame 3 and the door stop 12 in a second recess 17. Additionally, it is preferred that the mating surfaces of the frame 3 and door stop 12 be bare, e.g., unpainted to maintain their conductivity. If desired, the surfaces may have a conductive galvanized finish to prevent corrosion. Preferably they have a conductive strip along their surfaces which insures that the mating surfaces are in conductive engagement with each other. Such a strip is known as CHO-FOIL ® and/or CHO-MASK ® conductive tapes available from Chomerics, Inc. Alternatively, the frame 3 and door stop 12 may be formed of one piece of material, though this may be difficult or costly to manufacture.

The door 2, frame 3, and door stop 12 are all formed of an electrically conductive material, such as steel, including stainless steel; aluminum; or treated steel or treated aluminum. The frame 3 and door stop 12 are preferably of a tubular design, i.e., hollow, for weight and cost considerations. The door 2 preferably is a clad design, i.e., the outer surface of the door is formed of the selected electrically conductive material as described above. The door may be of a hollow core design, or of a filled core design. If the latter, it is preferred that the core filler is lightweight, rigid and supportive. Suitable materials include, for example, polystyrene and polyurethane foams, and honeycomb materials of metal, plastic, or resin impregnated materials.

The inner surface of the door which contacts the conductive gasket or compression stop should be conductive in a manner similar to the mating surfaces between the frame 3 and door stop 12. The inner surface may be galvanized, although it is preferred that a conductive strip, such as CHO-FOIL ® or CHO-MASK ®, available from Chomerics, Inc., be used on that portion of the door.

The conductive gasket is retained within the first recess of the door stop and extends around the entire side and top of the frame to prevent the movement of RFI/EMI signals through the space between the door 2 and the door stop 12 when the door 2 is in its closed position.

The conductive gasket 15 should require a low closure force to suitably engage its surface with that of the door 2. One preferred gasket is shaped in the form of a "V" which allows for a low application of closure force to obtain an adequate conductive seal. The required closure force of the preferred gasket is less than five (5) pounds of force per linear inch, more preferably, less than three (3) pounds of force per linear inch and most preferably less than one (1) pound of force per linear inch.

One such preferred conductive gasket useful in the present invention is a filled elastomeric material shown in FIG. 3 and sold by Chomerics, Inc. under the trademark, CHO-SEAL ® as the "Y" type gasket. The CHO-SEAL ® Y type gasket is a conductive silicone or fluorosilicone gasket having two arms which extend outwardly from a center portion in a manner similar to that of the small letter Y. One arm is at an angle to the plane of the other arm and center arm and is movable toward the other arm with very low amounts of force. The conductive filler may include but is not limited to a noble metal coated glass, such as silver coated glass; a noble metal coated particle such as silver coated copper, silver coated aluminum or silver coated plastic, a solid noble metal particle or flake, such as silver flake, a coated conductive metal particle such as nickel coated copper or a solid non noble metal such as copper, aluminum, nickel, tin or zinc.

Another preferred elastomeric conductive gasket that is useful in the present invention is known as the CHO-SEAL ® rounded "H" design and is sold by Chomerics, Inc.

Other conductive gaskets may also be used with the Present invention so long as they require a low closure force. For example, a "V" shaped metal gasket or a hollow wire mesh gasket may be used as the conductive gasket.

Alternatively, one can use the traditional metal finger stock or wire mesh gaskets. It has been found that these shielding materials work in the present door due to the use of the preferred hinges and the compression stop which limit the amount of friction and compression to which the materials are subjected. It is preferred however, not to use these traditional sealing materials as they tend to increase the closure force required to effectively close the door.

The selected gasket is preferably attached to the door stop 12 by a removable device so that the replacement of the gasket, when and if required, can be done quickly and without a need to dismantle the door assembly. Preferred means for attaching the gasket include a clip, as is shown in FIG. 3, or a conductive pressure sensitize adhesive applied to the surface of the gasket which mates with the surface of the first recess, and similar retaining means.

If however, one wished to permanently secure the gasket within the first recess, one could easily do so through the use of adhesives, welds, bolts and similar devices.

Regardless of the means used to attach the gasket in the recess, that means must provide the necessary conductive path between the door stop and the gasket. Thus, the retaining means must either itself be conductive or allow for the gasket to touch the surface of the first recess in a sufficient amount so that the conductive path is established and maintained.

Typical shielded door assemblies have high thresholds, i.e. raised thresholds similar in design to the door stops of the side and top members so that the door fits into a pocket along all four sides of the frame. The threshold of the present invention is of a low threshold design. By "low threshold" it is meant that the threshold is substantially flush with the floors of the surrounding enclosure so as to allow for easy and ready travel through the door assembly.

The threshold may contain a small stop means which may meet the bottom of the door, but such a stop means is not required and may be used if desired or required by the end user. The threshold may also be slightly inclined on one or both edges of the threshold so as to provide a ramp for the movement of personnel and equipment through the door assembly.

The threshold may be formed of any conductive material, preferably a metal such as stainless steel or galvanized steel, aluminum or galvanized aluminum, brass, copper, etc.

The space, if any, between the threshold 6 and the door 2 may be sealed both physically and electrically with any of the gaskets discussed above in relation to the rest of the doorframe 3. For example, an elastomeric "V" or "Y" type of conductive gasket may be used along the bottom of the door to form the required EMI/RFI shielding see FIG. 4A. Additionally, a metal finger stock type of gasket or a wire mesh gasket may be used in the present invention. This is particularly so, as the cam hinges raise and lower the door onto and away from the threshold, thus limiting the amount of friction and compression to which the gasket is exposed and thereby extending the life of the metal gasket.

Figure 4:
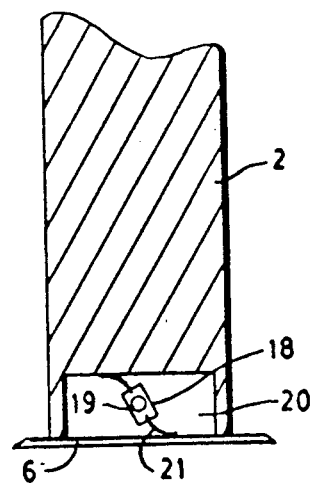
FIG. 4 is a cross sectional view taken along the section 4—4 of FIG. 1 viewed in the direction of the arrows and disclosing the door in its closed position.
Figure 4A:
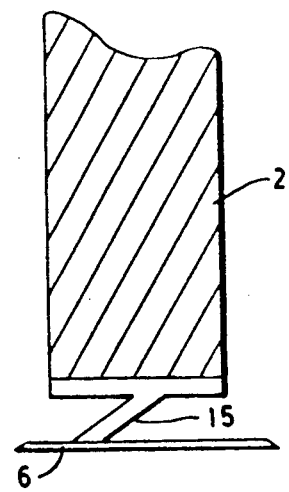
FIG. 4A shows an alternative arrangement for the bottom of the door in its closed position.

Alternatively, one could use a rotatable sealing means 18 as shown in FIG. 4. As can be seen from FIG. 4, an EMI/RFI conductive sealing means is mounted upon the longitudinal axis of a rotatable rod 19. This rotatable seal is preferably mounted in a hollowed out portion 20 of the door 2 nearest the threshold.

The sealing means consists of a flap-like or flipper-like blade 21 mounted to the rotatable rod 20. The blade 21 may be a one piece conductive rubber or metal sheet which is attached to the rod. Alternatively, it may be of a two piece construction. In that instance, the rod may contain two parallel grooves cut into its surface and running along its length. In these grooves, a suitable EMI/RFI blade of conductive elastomer or metal may be bonded, crimped, welded or otherwise secured to the rod such that the flipper will be retained on the rod and be electrically continuous with the rod.

The rod and blade are shown in their actuated position. In this instance, the rod has been rotated to a position such that the first blade arm is in contact with the door, preferably the top of the hollow and the second blade arm is in contact with the threshold of the door frame. In this position, there is electrical continuity between the door and door frame along the threshold's length.

An actuating means is used to rotate the rod and blade between the actuated and non-actuated position. One means for doing so is to use a gear driven device which rotates the sealing means to either position. The geared device can be electrically or mechanically driven and if desired, can be connected to the door handle so that as the door is unlatched, the seal is rotated to its non-actuated Position. In the non actuated position, the blade arms are essentially horizontal to and parallel with the plane of the threshold.

Another means for actuating the sealing means is by a camming means which could be connected to the door handle or could be separately actuated. As the cam is rotated, it causes the sealing means to move from one position to the other. If desired, the cam can be spring biased so that the sealing means is normally in its actuated position.

Likewise, a simple mechanical linkage, such as a push/pull rod attached to the rod and the door can be used to rotate the sealing means to and from its actuated position.

Preferably, however, the sealing means is automatically operated by a mechanical means so that the sealing means is always actuated when the door is closed. This ensures that an electrical failure or forgetfulness of the user does not void the door's shielding integrity.

Figure 5:
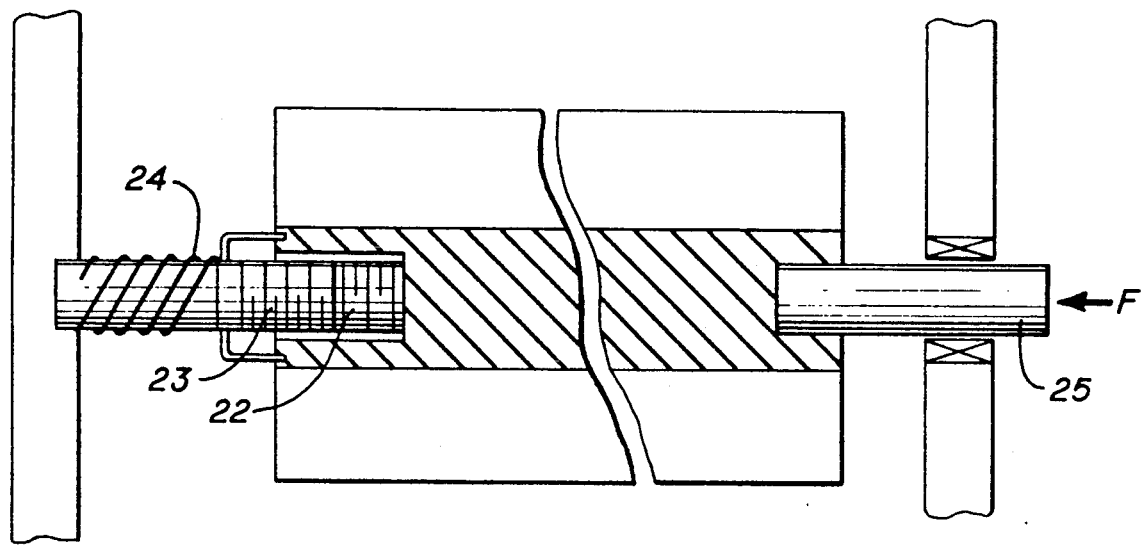
FIG. 5 is a cross sectional view taken along Section 5—5 of FIG. 1.

The preferred actuating means as shown in FIG. 5 comprises a threaded portion 22 on at least one end of the rod and a corresponding threaded portion 23 in the mounting means for the rod. A spring 24 surrounds and is attached to the rod so that as a linear force is imposed upon the unthreaded end 25 of the rod, the rod is forced to move inwardly along the threads of the holding means in a linear and rotational direction. Upon the relaxation of that linear force, the spring returns the rod to its original position, causing the rod to retreat in a linear and rotational direction. It is preferred that the sealing means be in its non-actuated when no linear force is being asserted. This position would correspond to when the door is in an opened position. As the door is closed, the unthreaded end of the rod contacts the door frame preferably along the hinge side and is subjected to a force which moves the rod inwardly. As the other end of the rod is threaded, it rides along the helical grooves of the threaded portion of the holding means and rotates the blade into its actuated position to establish EMI/RFI shielding between the threshold of the door frame and the door.

The rod should be formed of a conductive material that is strong, durable and wear resistant. Preferably, the rod is made of a conductive metal such as copper, aluminum, stainless steel or various metal alloys.

The blade is preferably formed of a conductive elastomer, such as conductive silicone or fluorosilicone. One suitable material is sold in sheet stock form under the trademark, CHO-SEAL ® by Chomerics, Inc. Alternatively, the blade can be formed of a thin, flexible metal strip such as copper, tinned copper, aluminum or steel.

Regardless of the material from which the blade is formed, the width of the blade arm should be sufficiently long so that when in the actuated position the outer portion of the blade respectively contact the door and the threshold.

If desired, the door assembly may also contain other features such as a shielded window or acoustical dampening materials. Such features are commonly used, are well known in the EMI/RFI shielding industry and are easily incorporated into the door assembly.

EXAMPLE

A door assembly according to the present invention was made of steel and mounted to an enclosure. Three cam hinges were mounted between the door and frame to allow the door to pivot freely. A Chomerics Y-type CHO-SEAL ® conductive gasket was mounted along the side and top members. An additional Y-type CHO-SEAL ® gasket was mounted to a metal flange along the bottom of the door such that when the door was in its closed position, the gasket formed an electrical pathway between the threshold and the door.

The door was subjected to a range of electromagnetic frequencies from 50 megahertz (MHz) to 1 gigahertz (GHz). The door exhibited a shielding effectiveness of 50 to 60 dbs at all of the tested frequencies.

The door was also subjected to a series of repeated openings and closings. After 10,000 cycles, the gaskets were found to have little, if no wear and had conductivity sufficient for EMI shielding.

This door has immediate uses in shielded enclosures such as computer rooms, communications facilities, etc. It would also be useful in any application which requires EMI/RFI shielding, a low threshold and an environmental seal.

While the present invention has been described in relation to its preferred embodiments, other embodiments can obtain the same result. Variations and modifications of the present invention will be obvious to one skilled in the art and it is intended to cover in the appended claims all such modifications and equivalents as fall within the true spirit and scope of this invention.

What is claimed is:

1. A shielded door assembly comprising:
   a) an electrically conductive frame having two side members, a top member and a bottom threshold, the top member and bottom threshold interconnecting the side members respectively along the top and bottom portion of the frame; the frame being mounted in an opening in an enclosure and being in electrical connection with the opening;
   b) an electrically conductive door stop attached to the two side members and top member of the frame and in electrical connection with the frame;
   c) an electrically conductive door pivotally secured to the frame and adapted for pivoting between an open and closed position, the door having an outer edge which is generally parallel to the frame and doorstop and cooperating with the doorstop when the door is in its closed position so that the door is in electrical connection with the doorstop;
   d) the doorstop having one or more electrically conductive resilient gaskets secured to a surface of the door stop with which the door is in electrical connection, the gaskets being secured to the doorstop and in electrical connection with the doorstop, the gaskets being adapted for engagement with the outer edge of the door when the door is in its closed position so as to establish an electrical connection between the door and the doorstop;
   e) the door having a recess along a bottom portion of the door, the recess being substantially parallel to the threshold of the frame, the recess containing a rotatable electrically conductive sealing device to establish an electrical contact between the threshold and the door when the door is in its closed position; and,
   f) a latching device mounted on the door for maintaining the door in its closed position.

2. The shielded door assembly of claim 1 wherein the frame, doorstop and door are formed of electrically conductive materials selected from the group consisting of steel, stainless steel, aluminum, treated steel and treated aluminum.

3. The shielded door assembly of claim 1 wherein the door is comprised of an outer layer of electrically conductive material and has a core which is hollow.

4. The shielded door assembly of claim 1 wherein the side members, top members and threshold of the frame are attached to each other so as to be in electrical connection with each other and with the opening of the enclosure.

5. The shielded door assembly of claim 1 wherein the frame and doorstop are tubular in form.

6. The shielded door assembly of claim 1 wherein the doorstop is secured to the frame by an electrically conductive securing means selected from the group consisting of screws, bolts, adhesives and welds.

7. The shielded door assembly of claim 1 wherein the doorstop as it is mounted to the frame forms a recess into which the door may pivotally move when its closed position.

8. The shielded door assembly of claim 1 wherein the door is pivotally secured to the door frame by a series of hinges.

9. The shielded door assembly of claim 8 wherein the hinges are cam or drop hinges.

10. A shielded door assembly comprising:
    a) an electrically conductive door frame generally rectangular in shape and designed to fit within an opening in an electrically conductive enclosure, the door frame having a top member, two side members depending downwardly from the top member, the two side members being spaced apart from and parallel to each other, and a threshold, spaced apart from and parallel to the top member, the threshold being attached to lower most portions of the two side member, the top member and two side members also containing an electrically conductive door stop along the innermost portions of the members;
    b) an electrically conductive door attached to one of the two side members by a series of hinges, and being adapted to pivotally move between an opened and closed position, the door being of such a size and shape so as to fit within the door frame and to engage a substantial portion of the door stop;
    c) the hinges which pivotally secure the door to the door frame having a means for raising and lowering the door from and to the threshold as the door is rotated between its closed and opened position;
    d) an EMI/RFI gasket mounted around the periphery of the door stop and in engagement with a surface of the door when the door is in its closed position;
    e) an EMI/RFI gasket along a bottom of the door so that it is in contact with the threshold of the door frame when the door is in a closed position, the gasket being subjected to limited friction and compression due to the ability of the hinges to raise and lower the door and the gasket thereon from and to the threshold as the door is rotated between its closed and opened positions; and f) a latch means for selectively securing the door in the door frame.

11. The shielded door assemby of claim 10 wherein the door frame, door and door stop are formed from a conductive metal selected from the group consisting of steel, stainless steel, treated steel, aluminum and treated aluminum.

12. The shielded door assembly of claim 10 wherein the means for raising and lowering the door is a cam or drop hinge.

13. The shielded door assembly of claim 10 wherein the EMI/RFI gasket mounted around the periphery of the doorstop is selected from the group consisting of metal finger stock, metal wire mesh gaskets and conductive elastomeric gaskets.

14. The shielded door assembly of claim 10 wherein the EMI/RFI gasket along the bottom of the door is same as the gasket mounted around the periphery of the doorstop.

15. A door and frame assembly for an enclosure that is shielded against leakage of electromagnetic or radio frequency radiation when the door is in its closed position comprising:

a) a door, generally rectangular in shape;

b) a door frame in which the door is mounted, the door frame forming a generally rectangular opening, the door frame having a stop means along its side and upper portions which stop means opposes the outer edges of the door so that the door, in its closed position, fits within the door frame and the outer edges of the door are adjacent to the stop means;

c) an EMI/RFI shielding means contained along the stop means and situated so as to be in contact with the door when the door is in its closed position;

d) an EMI/RFI shielding means mounted along a bottom portion of the door and situated so as to be in contact with the threshold of the door frame when the door is in its closed position; and e) a series of hinges mounted along one side of the door frame and connected to an edge of the door so that the door may pivot between a closed and an opened position relative to the door frame, the hinges having a means for raising the door relative to the door frame as the door is rotated from its closed to its opened position and for lowering the door relative to the door frame as the door is rotated from its opened to its closed position such that the amount of friction and compression to which the shielding means along the bottom of the door is limited thereby extending the life of the shielding means.

16. Am EMI/RFI shielded door and frame assembly comprising:

a) a frame assembly for mounting in an opening of an enclosure, the frame having a top portion and a bottom portion and two side portions positioned between the top and bottom portions so as to form a rectangular opening, the frame having a stop means formed along the inner periphery of the rectangular opening so as to define a pocket with the frame;

b) a door mounted by a series of hinges along one of the side members of the frame, the door being mounted such that when in its closed position, the door fits within the pocket defined in the frame;

c) an EMI/RFI shielding means mounted along the stop means and positioned to be in contact with the door when the door is in its closed position;

d) an EMI/RFI shielding device mounted along a lower most portion of the door so that when the door is in its closed position, the shielding device is in contact with the bottom portion of the door frame; and wherein the hinges are cam hinges capable of raising and lowering the door relative to the frame assembly, said hinges also limiting the amount of friction and compression applied the shielding device on the lowermost portion of the door due to the ability of the hinges to raise and lower the door as it is opened and closed.

17. A shielded door assembly comprising:

a) an electrically conductive door frame generally rectangular in shape and designed to fit within an opening in an electrically conductive enclosure, the door frame having a top member, two side members depending downwardly from the top member, the two side members being spaced apart from and parallel to each other, and a threshold, spaced apart from and parallel to the top member, the threshold being attached to lower most portions of the two side members, the top member and two side members also containing an electrically conductive door stop along the innermost portions of the members;

b) an electrically conductive door attached to one of the two side members by a series of hinges, and being adapted to pivotally move between an open and closed position, the door being of such a size and shape so as to fit within the door frame and to engage a substantial portion of the door stop;

c) the hinges which pivotally secure the door to the door frame having a means for raising and lowering the door from and to the threshold as the door is rotated between its closed and opened position;

d) an EMI/RFI gasket mounted around the periphery of the door stop and in engagement with a surface of the door when the door is in its closed position;

e) an EMI/RFI gasket along the bottom of the door, formed of a rotatable EMI/RFI seal, the seal having a rod rotatably mounted adjacent the bottom of the door and a flaplike conductive blade extending outwardly from the rod, the blade being of such a length that when rotated to its activated position, the blade establishes a conductive pathway between the door and the threshold; and f) a latch means for selectively securing the door in the door frame.

* * * * *